United States Patent [19]

Sutton et al.

[11] Patent Number: 5,374,516
[45] Date of Patent: Dec. 20, 1994

[54] AVIDIN-AND BIOTIN IMMOBILIZED REAGENTS AND METHODS OF USE

[75] Inventors: Richard C. Sutton; Brent A. Burdick; Susan J. Danielson, all of Rochester; Harold C. Warren, III, Rush; Brian A. Snyder; Gregory J. McClune, both of Rochester; Annie L. Wu, Penfield, all of N.Y.

[73] Assignee: Eastman Kodak Company, Rochester, N.Y.

[21] Appl. No.: 315,086

[22] Filed: Feb. 24, 1989

Related U.S. Application Data

[63] Continuation-in-part of Ser. No. 136,165, Dec. 18, 1987, abandoned.

[51] Int. Cl.$^5$ .............. G01N 33/545; G01N 33/546
[52] U.S. Cl. ......................... 435/5; 428/403; 428/407; 422/57; 436/531; 436/532; 436/533; 436/534; 436/536; 436/541; 525/328.5; 525/333.3; 526/286
[58] Field of Search ................ 422/56, 57; 436/531–534, 536, 541, 800; 435/5; 428/403, 407; 526/286, 317.1, 318.4; 525/328.5, 333.3

[56] References Cited

U.S. PATENT DOCUMENTS

| | | | |
|---|---|---|---|
| Re. 31,712 | 10/1984 | Giese | 428/407 |
| 4,259,313 | 3/1981 | Frank et al. | 424/8 |
| 4,298,685 | 11/1981 | Parikh et al. | 435/7 |
| 4,434,150 | 2/1984 | Azad et al. | 424/1.1 |
| 4,486,530 | 12/1984 | David et al. | 435/7 |
| 4,496,654 | 1/1985 | Katz et al. | 435/7 |
| 4,582,810 | 4/1986 | Rosenstein | 436/528 |
| 4,605,735 | 8/1986 | Miyoshi et al. | 536/27 |
| 4,703,018 | 10/1987 | Craig et al. | 436/518 |
| 4,828,978 | 5/1989 | Warren, III et al. | 436/533 |
| 4,997,772 | 3/1991 | Sutton et al. | 422/56 |

FOREIGN PATENT DOCUMENTS 139489  2/1985  European Pat. Off. .

OTHER PUBLICATIONS

*Research Disclosure*, publication 25611, Aug., 1985.
Hofmann et al, *Biochem.*, 21, pp. 978–984 (1982).
Odell et al, *Clin. Chem.* 32(10), pp. 1873–1878 (1986).
Manning et al, *Biochemistry*, 16(7) pp. 1364–1370 (1977).
Syvanen et al, *Nucleic Acids Research* 14(12) pp. 5037–5044.

*Primary Examiner*—David Saunders
*Assistant Examiner*—Christopher L. Chin
*Attorney, Agent, or Firm*—J. Lanny Tucker

[57] ABSTRACT

Reagents have been prepared from water-insoluble polymeric particles to which are covalently attached avidin, biotin or an avidin or biotin derivative. The polymeric particles comprise a polymer on at least the outer surface which is derived from at least one ethylenically unsaturated monomer having a reactive activated 2-substituted ethylsulfonyl, vinylsulfonyl or active halogen atom. Covalent attachment of avidin, biotin or an avidin or biotin derivative is effected either directly or indirectly through these reactive groups. The resulting reagent is useful in analytical elements and various analytical methods including agglutination and sandwich assays. The immobilized avidin, biotin or derivative can be used to complex with the corresponding biotin or avidin molecule which may be conjugated to a compound of biological interest.

25 Claims, No Drawings

AVIDIN-AND BIOTIN IMMOBILIZED REAGENTS AND METHODS OF USE

RELATED APPLICATION

This application is a continuation-in-part of U.S. Ser. No. 136,165, filed Dec. 18, 1987, now abandoned.

FIELD OF THE INVENTION

The present invention relates to water-insoluble reagents which are useful in various analytical procedures. It also relates to analytical elements and methods using these reagents.

BACKGROUND OF THE INVENTION

There is a continuous need in medical practice, research and diagnostic procedures for rapid, accurate, quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, seminal fluids and other biological fluids has to be determined in an accurate and rapid fashion for suitable diagnosis or treatment.

To provide such determinations, various methods have been devised for isolating and identifying biological substances employing specific binding reactions between the substance to be detected and receptors reactive with that substance. Radioactive or enzyme labels have been used to detect the resulting reactive complex.

One particular type of test which has been developed is an agglutination test which is useful for the detection of antigens which have multiple sites for antibody reactivity. In such a test, anti-body molecules can be bound in a suitable fashion to water-insoluble particles. Antibody-antigen reaction at multiple sites causes the particles to agglutinate and precipitate. Suitable separation and detection means have been devised to make the agglutinate readily observable, including for example, the use of particles containing a tracer material as described in copending U.S. Ser. No. 98,583, filed Sept. 18, 1987 by Sutton, Littlehale and Danielson, now U.S. Pat. No. 4,997,772 and in references cited therein.

Another useful method for detecting biological substances in fluids is what is known in the art as a "sandwich" assay. Such an assay involves "sandwiching" the compound of interest (such as an antigen) with two or more receptor molecules (such as antibodies) which complex with the compound at different and noninterfering sites. Examples of such assays are described, for example, in U.S. Pat. No. 4,486,530 (issued Dec. 4, 1984 to David et al). In most sandwich assays, one or more of the receptor molecules are suitably immobilized on an insoluble carrier such as small particles, membranes, plates, test wells or similar objects.

Attachment of antibodies or receptor molecules to insoluble carrier materials has been achieved in the past in a number of ways. Early work relied on adsorption of the molecules, but it was realized that adsorption is generally not a strong method of attachment. Later researchers found that the molecules could be covalently attached by reaction of certain functional groups of the molecules with specially designed reactive groups on the carrier material. For example, proteins have been attached by reacting carboxy groups of particles or supports with an activating compound which renders the groups reactive with amino groups of a protein. Carbodiimides are examples of useful activating compounds.

Avidin is a protein found in egg whites. Biotin (hexahydro-2-oxo-1H-thieno[3,4]imidazole-4-pentanoic acid), also known as Vitamin H, is a relatively small water-soluble molecule. These materials are known to react specifically with each other to form a very strong and stable complex in which each of the four subunits of avidin binds a biotin molecule. This strong binding is maintained even when either biotin or avidin or both are bound covalently to other materials. The reaction has been used to enhance agglutination of erythrocytes and provided researchers with a means for various biochemical and diagnostic studies.

U.S. Pat. No. 4,298,685 (issued Nov. 3, 1981 to Parikh et al) describes a competitive immunoassay in which antibodies conjugated to biotin are allowed to compete with the unknown analyte and a known quantity of enzyme-labeled analyte. The amount of antibody-analyte complexes is readily determined by insolubilizing the complexes by adding avidin attached to a carrier material. Avidin is bound to a solid support such as particles, filter paper, glass or plastic object by covalent attachment, for example covalent attachment to benzoquinone-activated sepharose.

U.S. Pat. No. 4,582,810 (issued Apr. 15, 1986 to Rosenstein) and PCT Publication 84/03358 (published Aug. 30, 1984) describe the attachment of avidin to latex particles having free carboxyl groups on their surfaces. As described therein, the conventional procedure for covalently attaching avidin to the particles involves the use of a water-soluble carbodiimide in an activation step. While producing reagents, this procedure tends to activate the exposed reactive groups of the protein avidin as well as the carboxyl groups on the particles. The result is intramolecular and intermolecular crosslinking or polymerization of avidin, and a significant portion of the reagent is impaired from complexation with biotin. In addition, there may be premature agglutination of the insolubilized reagent due to the cross-reactivity of the activating compound. These problems present a serious economic loss as well as an impairment of diagnostic sensitivity. It has also been evident that carbodiimides provide a reactive intermediate for avidin attachment which is unstable and must be used immediately.

Various other reagents have been prepared with particles having reactive groups such as epoxides, aldehydes, amino groups and diazonium salts. All of these groups have disadvantages. Epoxide groups are not stable, so that the particles cannot be stored for very long. Particles having aldehyde groups generally tend to agglutinate prematurely. The aldehyde groups also prematurely oxidize, thereby losing binding activity. Particles with amine groups are like the carboxylated materials by requiring an additional activation step for attachment. Diazonium compounds are unstable and therefore undesirable to work with.

Immunological compounds are immobilized on polymer particles having reactive activated 2-substituted ethylsulfonyl and vinylsulfonyl groups to form useful immunological reagents as described in copending U.S. Ser. No. 81,206 filed Aug. 3, 1987 by Sutton and Danielson, now abandoned. In some instances, however, it is not advisable to directly attach immunological compounds to the particles. For example, direct attachment may deactivate the immunological compounds. Yet, it is desired to strongly attach those compounds to the particles.

Hence, reagents which are composed of avidin or biotin covalently attached to a water-insoluble particle would be very useful in diagnostic methods. However, it would be desirable to have such reagents which are readily prepared in an efficient manner and under conditions which are not limiting and which do not reduce sensitivity or generate other undesirable results. It would be particularly desirable to avoid the use of conventional carbodiimide chemistry for attachment whereby premature crosslinking and agglutination are prominent. It would also be desirable to have reagents for insolubilizing immunological species without directly attaching the species to the insoluble carrier material. Yet the resulting attachment should be stronger than that achieved through mere adsorption.

SUMMARY OF THE INVENTION

The problems noted above with conventional reagents have been overcome with a water-insoluble reagent comprising:

a polymeric particle comprising a polymer on at least its outer surface which is derived from one or more ethylenically unsaturated polymerizable monomers, at least one of which monomers has reactive groups which are selected from the group consisting of activated 2-substituted ethylsulfonyl, vinylsulfonyl or an active halogen atom, the particle being covalently attached through the reactive groups on the outer surface of the particle to a specific binding ligand selected from the group consisting of avidin, biotin or an avidin or biotin derivative.

This invention also provides an element comprising an absorbent carrier material having one or more zones, and containing in one or more of the zones the water-insoluble reagent described above.

Further, a method for the determination of a compound of biological interest in an aqueous liquid comprises:

A. contacting the liquid with the water-insoluble reagent described above,
B. forming a reaction product of the reagent with the biological compound, and
C. determining the amount of the biological compound as a result of the presence of the reaction product.

The present invention provides stable reagents which can be used in a variety of analytical and diagnostic procedures to great advantage. The polymer particles used to prepare the reagents have readily available functional groups which readily react with avidin, biotin or avidin or biotin derivatives. The useful functional groups include an activated 2-substituted ethylsulfonyl group, vinylsulfonyl group or a group containing an active halogen atom. The reaction between avidin or an avidin derivative with particles containing these groups can be accomplished without the need for activators such as carbodiimides and additional activation steps. Therefore, the problems associated with the activation of carboxy groups (that is premature crosslinking and agglutination) are generally avoided.

In addition, preferred reagents of this invention wherein the particles have reactive vinylsulfonyl and activated 2-substituted ethylsulfonyl groups exhibit further advantages in that they can be reacted under mild pH conditions and low temperatures. Hence, the conditions of attachment are not as critical and lower temperatures, shorter reaction times and flexible mixing conditions can be employed without sacrificing sensitivity. Yet the reagent of this invention can be used to strongly attach immunological or other specific binding compounds to an insoluble carrier material.

DETAILED DESCRIPTION OF THE INVENTION

The present invention provides a reagent for use in analytical methods and elements whereby a detectable complex is obtained using the high specific binding affinity of avidin for biotin. The methods can quickly provide a determination so that the assay can be performed in a doctor's office or in a consumer's home to provide immediate results. The test can be used to detect the presence or absence of a compound of biological interest in an aqueous liquid, such as a biological fluid.

A compound of biological interest is defined herein as any biological or chemical compound which has one or more sites for complexing with a corresponding specific binding receptor molecule. In one embodiment, the compound of biological interest may be avidin or biotin which can then be detected with the reagent of this invention containing the corresponding receptor therefor. For example, to detect biotin in a fluid, a reagent having avidin molecules attached thereto is used.

Compounds of biological interest can also be defined as ligands which specifically complex with a corresponding receptor molecule which is not biotin or avidin. For example, the compound could be an immunological species which is (1) any substance which, when presented to an immunocompetent host, will result in the production of a specific antibody capable of binding with that substance, or (2) the antibody so produced, which compound participates in an antigen-antibody reaction. In such embodiments, avidin, biotin or an avidin or biotin derivative is suitably attached to the receptor molecule which reacts specifically with the biological compound.

Representative ligands detectable with the present invention include primary amines, amino acids, peptides, polypeptides, proteins, lipoproteins, glycoproteins, drugs, haptens, enzymes, steroids, lipids, nucleic acids, hormones, vitamins, polysaccharides, glycolipids, alkaloids, organisms (bacteria, protozoa, fungi, viruses, rickettsia and the like) and components thereof, blood components, tissue and organ antigens and other materials known to one skilled in the art. In some instances, the ligand is an antibody which is directed against a drug, hormone, antibiotic or other compound having antigenic properties. Alternatively, the ligand can be an antigenic material (including mono- or multivalent or multideterminant antigens). In still another embodiment, the immunological species is an antibody which is directed against another antibody (that is, an anti-antibody). Both monoclonal and polyclonal antibodies can be used, and they can be whole molecules or various fragments thereof.

The reagent of the present invention is prepared by covalently attaching avidin, biotin or a derivative of either to water-insoluble polymeric particles of specific composition. The attachment is achieved through amino or sulfhydryl groups of the avidin, or avidin or biotin derivative which are available for reaction directly with reactive groups on the outer surface of the particles. "Direct" attachment means that the avidin or avidin or biotin derivative molecule is directly reacted with the particle groups. Alternatively, the material can be chemically modified to provide reactive sites for attachment as long as such modification does not adversely affect the sites where avidin and biotin will complex with each other. For example, biotin cannot be attached directly to such particles, but suitable biotin derivatives having suitable reactive groups (such as succinimidooxycarbonyl, maleimidooxycarbonyl or N'-bromoacetylhydrazinocarbonyl) can be attached to particles pretreated with a protein such as casein to provide amine groups that react with the biotin derivative. Biotin derivatives having reactive amine or sulfhydryl groups can be directly attached to the particles. In addition, avidin, biotin, or a derivative of either can be "indirectly" attached through a linking moiety which can be a protein, peptide, polypeptide, diamine or dimercaptan.

Avidin and biotin derivatives which can be used to prepare the reagents of this invention include streptavidin, succinylated avidin, monomeric avidin, biocytin (that is, biotin-ε-N-lysine), biocytin hydrazide, amine or sulfhydryl derivatives of 2-iminobiotin and biotinyl-ε-aminocaproic acid hydrazide.

Biotin derivatives, such as biotin-N-hydroxysuccinimide ester, biotinyl-ε-aminocaproic acid-N-hydroxysuccinimide ester, sulfosuccinimidyl 6-(biotin amido)-hexanoate, N-hydroxysuccinimideiminobiotin, biotin-bromoacetylhydrazide, p-diazobenzoyl biocytin and 3-(N-maleimidopropionyl)biocytin, can also be attached to linking proteins after such proteins have been suitably attached to the polymeric particles.

The particles used in preparing the present invention comprise one or more polymers each of which is prepared from one or more ethylenically unsaturated polymerizable monomers which are described below in more detail. At least one of such monomers provides the desired reactive groups on at least the surface of the particles. In some embodiments, the particles are homogeneous, that is, they are composed of the same polymer throughout. In other embodiments, the particles can be composed of two or more polymers, for example as core/shell particles (described for example in U.S. Ser. No. 98,583, noted above, and in U.S. Pat. No. 4,401,765, issued Aug. 30, 1983 to Craig et al), or as graft copolymers as described for example in U.S. Pat. No. 3,700,069 (issued Oct. 24, 1972 to Tregear et al).

The polymeric particles are generally water-insoluble latex particles having an average particle size greater than about 0.01 micrometers. Preferably they have an average particle size in the range of from about 0.01 to about 5 micrometers.

As described above, the polymeric particles useful in the practice of this invention comprise at least one polymer derived from at least one α,β-ethylenically unsaturated polymerizable monomer having one or more of the reactive groups selected from the group consisting of activated 2-substituted ethylsulfonyl, vinylsulfonyl or an active halogen atom.

Monomers having an active halogen atom include vinyl chloroacetate, vinyl bromoacetate, haloalkylated vinyl aromatics (for example, chloromethylstyrene or bromomethylstyrene), haloalkyl acrylic or methacrylic esters (for example, chloroethyl methacrylate, 3-chloro-2-hydroxypropyl methacrylate and 3-chloropropyl acrylate), N-{3-[N'-(3-chloropropionyl)ureido]propyl}methacryl amide, 4-(3-chloropropionamido)styrene, 4-[N'-(3-chloropropionyl)ureido]styrene, 2-(3-chloropropionamido)ethyl methacrylate, N-[3-(3-chloropropionamido)propyl]methacrylamide, N-(3-chloroacetamidopropyl)methacrylamide, N-(2-chloroacetamidoethyl)methacrylamide, 4-chloroacetamidostyrene, 4-chloroacetamidomethylstyrene, N-[3-(N'-chloroacetylureido)propyl]methacrylamide, N-[2-(N'-chloroacetylureido)ethyl]methacrylamide, 4-(N'-chloroacetylureido)styrene, m- & p-(N'-chloroacetylureidomethyl)styrene, and others known to one skilled in the art. The haloalkylated vinyl aromatics, for example those having active haloalkyl groups of 1 to 3 carbon atoms, are preferred when the active halogen atom is used as the reactive group. Chloromethylstyrene is most preferred.

As noted above, the monomers having active halogen atoms exhibit many advantages over the materials of the art. However, monomers having activated 2-substituted ethylsulfonyl and vinylsulfonyl groups possess additional advantages in that proteins can be attached to the polymers under milder conditions and require less process control during manufacture. This renders manufacture more efficient and less costly. A number of representative monomers having the requisite pendant groups are known in the art, including those disclosed in U.S. Pat. Nos. 4,161,407 (issued Jul. 17, 1979 to Campbell) and 4,548,870 (issued Oct. 22, 1985 to Ogawa et al).

Preferred activated 2-substituted ethylsulfonyl and vinylsulfonyl monomers can be represented by the formula (I):

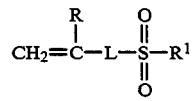

wherein
R is hydrogen or substituted or unsubstituted alkyl (generally of 1 to 6 carbon atoms, such as methyl, ethyl, isopropyl or hexyl. Preferably, R is hydrogen or methyl.

$R^1$ is —CH=CHR$^2$ or —CH$_2$CH$_2$X wherein X is a leaving group which is displaced by a nucleophile or is eliminated in the form of HX by treatment with a base (such as halo, acetoxy, alkylsulfonyloxy such as methylsulfonyloxy, arylsulfonyloxy such as p-tolylsulfonyloxy, trialkylammonio, for example, a trimethylammonio salt or pyridinio salt). $R^2$ is hydrogen, substituted or unsubstituted alkyl (generally of 1 to 6 carbon atoms as defined for R), or substituted or unsubstituted aryl (generally of 6 to 12 nuclear carbon atoms, such as phenyl, naphthyl, xylyl or tolyl). Preferably, $R^1$ is —CH$_2$CH$_2$X. This group, which is an activated 2-substituted ethyl group, can be substituted with any group which does not impair the displacement of the leaving group X.

L is a linking group which can be a substituted or unsubstituted alkylene generally having 1 to 20 carbon and hetero atoms in the backbone. This definition of alkylene is meant to include alkylene groups interrupted or terminated with oxy, thio, —NR$^3$— [wherein R$^3$ is hydrogen, substituted or unsubstituted alkyl of 1 to 6 carbon atoms (such as methyl, chloromethyl or 2-hydroxyethyl) or substituted or unsubstituted aryl of 6 to 10 carbon atoms (such as phenyl, naphthyl or xylyl)], ester (—COO—), amide (—CONH—), urylene

sulfonyl (—SO₂—), carbonate, sulfonamide, azo, phosphono or other similar groups. Representative alkylene groups include methylene, ethylene, isobutylene, hexamethylene, carbonyloxyethyleneoxycarbonylethylene, methylenebis(iminocarbonyl)ethylene, carbonyloxydodecylenecarbonyloxyethylene, carbonyliminomethyleneiminocarbonyliminoethylene, carbonyliminomethyleneiminocarbonylethylene and other groups described or suggested by U.S. Pat. Nos. 4,161,407 and 4,548,870, noted above.

L can also be substituted or unsubstituted arylene generally having 6 to 12 nuclear carbon atoms. Representative arylene groups include phenylene, tolylene, naphthylene and others noted in the patents mentioned above. Also included in this definition of L are divalent groups which are combinations of one or more of each of the alkylene and arylene groups defined above (for example, arylenealkylene, alkylenearylenealkylene and others readily determined by one of ordinary skill in the art), as well as such combinations which are interrupted or terminated by one or more amide or ester groups (for example, carbonyliminoarylenealkylene). Preferably, L is substituted or unsubstituted phenylenealkylene [for example, substituted with one or more alkyl groups (as defined for R), alkoxy groups (generally of 1 to 6 carbon atoms, for example, methoxy, propoxy or butoxy) or halo groups], carbonyliminoarylenealkylene (wherein arylene and alkylene are defined above), or carbonyliminoalkyleneiminocarbonylalkylene (wherein alkylene are defined above).

Representative useful monomers include m & p-(2-chloroethylsulfonylmethyl)styrene, m & p-[2-(p-tolylsulfonyloxy)ethylsulfonylmethyl]styrene, m & p-vinylsulfonylmethylstyrene, N-[m & p-(2-chloroethylsulfonymethyl)phenyl]acrylamide, and N-[2-(2-chloroethylsulfonyl)ethylformamidomethyl]acrylamide. The first monomer is preferred.

One or more of the monomers described above can be polymerized individually or in combination to form homo- or copolymers. Alternatively, and preferably, one or more of them are copolymerized with at least one other ethylenically unsaturated polymerizable monomer. Generally such monomers provide various desirable properties such as hydrophobicity, dispersibility or other features. Preferred polymers can be represented by the formula (II):

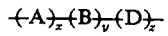 (II)

wherein —A— represents recurring units derived from one or more hydrophobic ethylenically unsaturated monomers, —B— represents recurring units derived from one or more ethylenically unsaturated monomers having the requisite reactive groups described above, and —D— represents recurring units derived from one or more ethylenically unsaturated monomers which are different than those represented by —A— or —B—.

In formula (II), x is from 0 to about 99.9 mole percent, y is from about 0.1 to 100 mole percent, and z is from 0 to about 20 mole percent. Preferably, x is from about 45 to about 99.5 mole percent, y is from about 0.5 to about 50 mole percent, and z is from 0 to about 10 mole percent.

Monomers from which the —A— recurring units are derived, both in general and in preferred embodiments, are hydrophobic and form homopolymers that are insoluble in water. Preferably, these monomers have aromatic groups. Representative hydrophobic monomers include, but are not limited to, styrene and styrene derivatives (for example, 4-vinyltoluene, 2,5-dimethylstyrene, 4-t-butylstyrene, 2-chlorostyrene and others known in the art), acrylic and methacrylic acid esters and amides (for example, n-butyl acrylate, propyl methacrylate, methyl acrylate, methyl methacrylate, ethyl methacrylate, 2-ethylhexyl methacrylate, N-phenylacrylamide and others known in the art), acrylonitrile and vinyl acetate.

This polymer can be crosslinked, if desired, in any suitable fashion. One method is to incorporate a small amount, that is up to about 10 mole percent, and preferably from about 0.3 to about 5 mole percent, of a monomer having two or more ethylenically unsaturated polymerizable groups. These monomers are included among the hydrophobic monomers from which A is derived. Representative monomers are described in Research Disclosure, publication 19551, July, 1980, page 304, and include for example, divinylbenzene, ethylene dimethacrylate, N,N'-methylenebisacrylamide, 2,2-dimethyl-1,3-propylene diacrylate, allyl acrylate, ethylidyne trimethacrylate and ethylene diacrylate. Cross-linking with such monomers, however, reduces the swellability of polymers, especially of the core of core/shell polymers caused by the organic solvent used in preferred techniques for imbibing tracer materials into polymeric particles. Therefore, crosslinking is generally limited to small amounts as required to impart water-insolubility.

Preferred monomers from which the —A— recurring units are derived are vinyl aromatic monomers, especially styrene and styrene derivatives.

The monomers from which the —B— recurring units are derived are those having the reactive groups described above.

Monomers from which the —D— recurring units are derived include monomers different than those from which —A— and —B— are derived. Specifically, the —D— recurring units are derived from monomers which impart aqueous dispersion stability to the particles or other properties. Representative monomers include, but are not limited to, anionic monomers such as sodium 2-acrylamido-2-methylpropanesulfonate, acrylic acid, methacrylic acid, 2-carboxyethyl acrylate, styrene sulfonic acid, potassium salt and m & p-carboxymethylstyrene and other ethylenically unsaturated polymerizable sulfonates, carboxylates, sulfates and phosphonates, other hydrophilic but nonionic monomers, such as 2-hydroxyethyl acrylate and 2-hydroxyethyl methacrylate and others known to one skilled in the art.

Preferred monomers from which the —D— units are derived are acrylic acid, methacrylic acid, sodium 2-acrylamido-2-methylpropanesulfonate, m & p-carboxymethylstyrene and p-styrenesulfonic acid, potassium salt.

Representative polymers of the monomers described above include the following: poly(m & p-chloromethylstyrene), poly(styrene-co-m & p-chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[m & p-(2-chloroethylsulfonylmethyl)phenyl]acrylamide} (99.3:0.7 molar ratio), poly(m & p-chloromethylstyrene-co-methacrylic acid)(95:5, 98:2 and 99.8:0.2 molar ratio), poly(styrene-co-m & p-chloroethylsulfonylmethylstyrene-co-methacrylic acid)(93.5:4.5:2 molar ratio), poly{styrene-co-N-[m & p-(2-chloroethylsulfonylmethyl)phenyl]acrylamide-co-methacrylic acid}(97.3:0.7:2 molar ratio), and poly(styrene-co-m & p-chloromethylstyrene)(70:30 molar ratio).

As noted above, the particles useful in the practice of this invention can be homogeneously composed of one of the polymers described above, or a mixture thereof. Alternatively, the polymers described above can be an outer graft or shell of a grafted copolymer or core-shell particle, respectively. Useful core-shell polymers are described, for example, in U.S. Ser. No. 98,583, noted above now U.S. Pat. No. 4,997,772.

The polymeric particles can be prepared using any suitable polymerization technique, including emulsion (including batch, semi-continuous and continuous) and suspension polymerization techniques, graft copolymerization, and others known to one skilled in the polymer chemistry art. Emulsion polymerization is preferred as it can be used to provide particles without the use of surfactants or emulsifiers as described for example in U.S. Pat. No. 4,415,700 (noted above) and *Research Disclosure* is a publication available from Kenneth Mason Publications, Ltd., The Old Harbourmaster's, 8 North Street, Emsworth, Hampshire P010 7DD, England. Continuous emulsion polymerization is the most preferred technique, as described in the noted *Research Disclosure* publication. Other details of preparatory methods can be found in U.S. Pat. Nos. 4,161,407 and 4,548,870, noted above.

Staged emulsion polymerization can be used to provide a core-shell polymer composed of two different polymers. Emulsion polymerization of the core is carried to substantial completion by continuously adding reactants to a reaction vessel under standard conditions. Monomers and catalysts needed to make the shell polymer are then continuously added to the vessel containing the latex of the core polymer. In this manner, the shell has a definite known composition rather than being a mixture of core and shell monomers. Representative details of preparing the core-shell polymeric particles useful in this invention are provided in U.S. Ser. No. 98,583 now U.S. Pat. No. 4,997,772, noted above.

The general procedure for preparing the reagent of this invention includes covalently attaching avidin, biotin or an avidin or biotin derivative to the particles using generally known reactions. With the active halogen atom, 2-substituted activated ethylsulfonyl and vinylsulfonyl groups, avidin or an avidin derivative can be directly attached to the particles. Biotin or derivatives thereof can be attached indirectly as noted above. Generally, the polymer particles are mixed with the material to be attached in an aqueous buffered solution (pH generally from about 7 to about 10) and a concentration of from about 0.01 to about 40 weight percent polymer particles (preferably from about 0.01 to about 10 weight percent). The amount of avidin, biotin or a derivative of either is at a weight ratio to polymer of from about 0.1:1000 to about 1:10, and preferably from about 1:100 to about 1:10. Mixing is carried out at a temperature in the range of from about 5° to about 50° C., and preferably at from about 5° to about 40° C., for from about 0.5 to about 48 hours. Any suitable buffer can be used. The details of a representative preparatory procedure are illustrated in Example 1 below.

The procedural details of direct and indirect attachment of avidin, biotin or derivatives thereof are known in the art.

The polymeric particles used in this invention can have a detectable tracer material associated therewith if desired. A tracer is a material which is detectable with the unaided eye or with appropriate equipment and techniques. The tracer material can be inside or outside of the particles. In one embodiment where the reagents are used in an agglutination assay, the tracer is preferably inside the particles. Useful tracers include, but are not limited to, radioisotopes which emit gamma rays, fluorescent compounds or dyes, bioluminescent compounds, chemiluminescent compounds, chromogens such as dyes and dye-formers which absorb in the visible or ultraviolet region of the electromagnetic spectrum, and others known to one skilled in the art. Particularly useful reagents having detectable tracers include those having core/shell polymers in which the tracer is in the core only. U.S. Ser. No. 98,583, noted above now U.S. Pat. No. 4,997,772, describes similar reagents. In other embodiments, the tracer is on the outside of the particles, either attached to the particles in some manner or as part of the avidin or biotin molecules.

The reagent of the present invention can be used in the determination (qualitative or quantitative measurement) of a biological compound in aqueous liquids. This determination can be made by merely determining the presence or absence of the compound, or by quantitatively determining the amount of compound. In particular, the invention can be used to assay biological fluids of animals, humans or plants, but preferably of humans. Such fluids include, but are not limited to, whole blood, plasma, sera, lymph, bile, urine, spinal fluid, seminal fluid, lacrimal fluid, vaginal secretions, sputum, perspiration and the like as well as stool specimens. It is also possible to assay fluid preparations of human or animal tissue such as skeletal muscle, heart, kidney, lungs, brains, bone marrow, skin and the like.

The present invention can be used to determine avidin, biotin or a derivative of either which is reactive with the corresponding moiety which is a part of the reagent of this invention. For example, the reagent can be comprised of avidin attached to a particle, and the compound to be determined is biotin or a derivative thereof with which the avidin is reactive.

Alternatively, the biological compound is a ligand other than avidin or biotin, such as an antibody or antigen, which has one or more sites for complexation with one or more receptor molecules. Such receptor molecules are usually immunologically reactive species. At least one of the receptor molecules is conjugated with avidin or biotin. The ligand can be complexed with the receptors, and the entire complex can be insolubilized by reaction of the conjugated avidin or biotin with the reagent of this invention. For example, the ligand can be Streptococcus A antigen, an antigen from chlamydial or gonococcal organisms, HTLV antigens or antibodies (for example, HTLV-I or HTLV-II), HIV antigens or antibodies (for example, HIV-I or HIV-II), thyroid stimulating hormone, apolipoproteins, human chorionic gonadotropin, leutinizing hormone, carcinoembryonic antigen, hepatitis antigen, herpes viruses and other biological and chemical compounds.

The reagent can be used in competitive binding immunoassays. Either bound (that is, complexed) or unbound (that is, uncomplexed) labeled materials can be determined. Physical separation of bound and unbound materials, if desired, can be carried out using any suitable separation technique. In using the analytical elements described below, either vertical or horizontal separation can be used.

In another embodiment, the reagent can be used in what are known in the art as immunometric assays, for example, "sandwich" assays. The details of such assays are provided in U.S. Pat. No. 4,486,530 (noted above). The reagent of the present invention is useful in such assays where the ligand to be determined has two or more epitopic sites for immunological reaction with two or more receptor molecules. The receptor molecules can be the same or different. The receptors are capable of immunologically reacting with the ligand at different sites. The result of the method is the formation of a ternary complex of the two distinct receptors with the ligand. At least one of the receptors is covalently attached to biotin or avidin (preferably biotin). The corresponding avidin or biotin molecule is attached to the particles described herein. The ternary complex is insolubilized when the avidin and biotin react, and the resulting insolubilized complex can be separated from unreacted material. The particles can be suitably labeled for detection, or one or more of the receptor molecules can be suitably labeled, such as with an enzyme. In a preferred immunometric assay, both receptors are distinct antibodies directed against an antigen, one of which antibodies is enzyme-labeled. they can be the same or different antibodies, whole or fragments, monoclonal or polyclonal.

The method of this invention can be used in either solution or dry assays. By solution assay is meant that the reagents are used in liquid suspension. In dry assays, the reagent is incorporated in a dry analytical element. The simplest element can be composed of an absorbent carrier material, for example, a thin sheet of a self-supporting absorbent or bibulous material, such as filter paper or strips, which has one or more zones, at least one zone containing the reagent of this invention. Other zones can be used to contain other useful reagents. Such elements are known in the art as test strips, diagnostic elements, dip sticks or diagnostic agents.

Useful absorbent carrier materials are insoluble and maintain their structural integrity when exposed to water or biological fluids such as whole blood or serum. Useful elements can be prepared from paper, porous particulate structures, porous polymeric films, cellulose, glass fibers, woven and nonwoven fabrics (synthetic and nonsynthetic) and the like. Useful materials and procedures for making such elements are well known in the art.

Preferably, the absorbent carrier material of the dry analytical element of this invention is a porous spreading zone. This zone can be self-supporting (that is, composed of a material rigid enough to maintain its integrity), but preferably it is carried on a separate support. Such a support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (fluorescence, transmission or reflectance spectroscopy). Useful supports can be prepared from paper, metal foils, polystyrene, polyesters, polycarbonates or cellulose esters.

The porous spreading zone can be prepared from any suitable fibrous or non-fibrous material or mixtures of either or both. The void volume and average pore size of this zone can be varied depending upon the use intended. Useful spreading zones can be prepared using materials and procedures described, for example, in U.S. Pat. Nos. 4,292,272 (issued Sep. 29, 1981 to Kitajima et al), 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760.

The elements can have two or more discrete zones, either in the same layer or superimposed. At least one of the zones is preferably a porous spreading zone. The other zones can be reagent zones or registration zones as those zones are known in the art, additional spreading zones, radiation-blocking or filter zones, subbing zones or barrier zones. The zones are generally in fluid contact with each other, meaning that fluids, soluble reactive materials and soluble reaction products can pass or be transported between superposed regions of adjacent zones. In other words, when the element is contacted with fluid, the reagents within the element become mixed and can readily interact. Preferably, each zone is a separately coated layer, although two or more zones can be separate areas in a single layer of the element.

Preferably, the reagent of this invention is used to detect a multivalent ligand such as the hormone, human chorionic gonadotropin (hCG), the presence of which in a woman's urine can be an early indicator of pregnancy. An assay for hCG is demonstrated in Example 1 below. This embodiment relating to hCG is presented for illustrative purposes, but it will be understood that the scope of this invention is not so limited. A biological sample (usually urine) suspected of containing the hormone is collected from a patient and contacted with the reagent of this invention. If the ligand is present, a reaction product is formed between the ligand and one or more receptor molecules therefor. One of the receptor molecules can be conjugated to either avidin or biotin which reacts with the reagent of this invention. For example, the reagent can have avidin molecules attached to the particles, which molecules react with biotin molecules which are conjugated with a receptor molecule (such as an antibody) for hCG. The amount of ligand is thereby determined by measuring the presence or amount of the resulting reaction product which is immobilized with the particles. Generally such detection is carried out by measuring the amount of detectable tracer in the complexed or uncomplexed materials.

The method of this invention can also be carried out in a disposable test device wherein a filtration membrane is used to separate complexed materials from uncomplexed materials. Such a device can have one or more wells into which a test sample containing a ligand is added for reaction with the appropriate reagents including the reagent of this invention. An example of such a test device is described and claimed in copending and commonly assigned U.S. Ser. No. 19,810 filed Feb. 27, 1987 by Hinckley now U.S. Pat. No. 4,870,007. Other variations of useful test devices would be within the purview of an ordinary worker skilled in the art.

The following examples illustrate the practice of the present invention.

EXAMPLE 1

Preparation of a Reagent

This example illustrates the preparation of a polymer latex and the attachment of avidin in the preparation of a reagent of the present invention.

Preparation of Polymer Latex

The three solutions outlined below were continuously added to a 1365 ml vessel containing deoxygenated water at 80° C. at the indicated rates:

Solution 1: Styrene (739 g), m & p-(2-chloroethylsulfonylmethyl)styrene (82 g) and 1-dodecanethiol (8.2 g) at 2.5 g/min. for 380 minutes.

Solution 2: Ammonium persulfate (19.7 g) and distilled, deoxygenated water (1152 g) at 2.14 g/min. for 380 minutes.

Solution 3: Sodium pyrosulfite (9.9 g) and distilled water (1152 g) at 2.27 g/min. for 380 minutes.

After 380 minutes, the reaction was stopped, yielding about 1218 g of latex at 33.4% solids. The latex was dialyzed for 3 days to yield a latex having 27.3% solids and a pH of 5. This latex was diluted to 13.5% solids. NMR analysis confirmed a 96:4 molar ratio of styrene to the second monomer. The resulting latex particles had an average diameter of about 0.67 $\mu$m as measured by transmission electron microscopy.

Covalent Attachment of Avidin

A sample (0.75 ml) of the latex described above was diluted to 20 ml with borate buffer (50 mmolar, pH 8.5) and avidin (5 mg, Sigma Chemical Co.) was subsequently added. The resulting suspension was agitated in an end-over-end fashion at 37° C. for 18 hours, followed by centrifugation. The supernatant was discarded and the particles washed once with buffer by centrifugation and resuspended in 10 ml borate buffer. Biotin binding analysis (that is, titration with tritium labeled biotin) indicated that avidin had been covalently attached to the particles ($7 \times 10^{-6}$ molar binding sites per 0.3% bead suspension) to form a reagent of the present invention.

EXAMPLE 2

Preparation of a Larger Sized Reagent

A reagent was prepared similar to that prepared in Example 1 except the polymeric particles in the latex had an average diameter of about 2.5 $\mu$m. A sample (0.65 ml at 15.5% solids) of purified latex was diluted to 10 ml with borate buffer (50 mmolar, pH 8.5) and avidin (1 mg, Sigma Chemical Co.) was added. The resulting suspension was agitated end-over-end at room temperature for 24 hours. Radiolabeled tracer analysis (avidin labeled with $^{125}$I) indicated 84% of avidin was covalently bound to the particles following washing of the beads three times.

EXAMPLE 3

Use of Reagent in the Determination of Human Chorionic Gonadotropin

This example demonstrates the use of the reagent of this invention is an assay to determine hCG. This example is taken from copending U.S. Ser. No. 136,211, filed on Dec. 18, 1987 by Smith-Lewis, now U.S. Pat. No. 4,870,007.

A test device as described in the just mentioned patent application was used to determine hCG in a urine sample in the following manner. This device contained a filter membrane consisting of a commercially available nylon membrane coated with succinylated casein. A conjugate (3 $\mu$g) of biotin and a monoclonal antibody directed to hCG was incorporated into the sample well of the test device in a coating with poly(acrylamide) (60 $\mu$g). A buffer, 3-(N-morpholino)propanesulfonic acid (2 mg, pH 7.2), was incorporated in a different location in the sample well.

A urine sample, prefiltered to remove impurities, and containing about 50 mI.U./ml of hCG, was added to the sample well followed by addition of a second monoclonal antibody to hCG which is labeled with horseradish peroxidase (40 $\mu$l of a $10^{-9}$ molar solution). A complex of antigen (hCG) and the two antibodies was formed in solution during a one minute incubation period at room temperature.

A sample of the immunoreactive reagent of this invention was then added to the well containing the complex. This sample contained 40 $\mu$l of a 0.42% dispersion of poly[styrene-co-m & p-(2-chloroethylsulfonylmethyl)styrene] particles to which avidin was attached. After this addition, fluid in the well was allowed to drain through the membrane of the test device, and a wash solution containing 0.1 molar sodium phosphate (200 $\mu$l) and sodium dodecylsulfate (10 mmolar) was added. A dye-providing composition (40 $\mu$l) was then added. It was prepared according to copending U.S. Ser. No. 136,166 filed Dec. 18, 1987 by McClune et al now U.S. Pat. No. 5,024,935. This composition comprised 2-(4-hydroxy-3,5-dimethoxyphenyl)-4,5-bis (4-methoxyphenyl)imidazole leuco dye (0.005% in 40 $\mu$solution), poly(vinyl pyrrolidone) (1%), diethylenetriaminepentaacetic acid (10 $\mu$molar) chelating agent, 4'-hydroxyacetanilide (5 mmolar) electron transfer agent, hydrogen peroxide (10 mmolar) in an aqueous solution buffered to pH 7 with sodium phosphate with a minor amount of methanol. After two minutes of reaction, a detectable dye was formed in the complex retained in the sample well on the membrane. The amount of dye was measured by converting the measured reflectance to transmittance ($D_T$) using conventional equipment and the Williams-Clapper transform (J. Opt. Soc. Am., 43, p. 595, 1953). The amount of measured dye was an indication of the presence of hCG in the urine sample tested.

EXAMPLE 4

Preparation of Reagent Using Particles Having Reactive Chloromethyl Groups

Poly(styrene-co-m & p-chloromethylstyrene) (77.3:22.7 molar ratio) particles having an average particle diameter size of 2.9 $\mu$m were prepared using a continuous emulsion polymerization procedure similar to that described in Example 1 above. A sample of the resulting latex (0.82 ml, 12.2% solids) was diluted with 20 ml of 0.05 molar borate buffer (pH 8.5, containing 0.01% thiomersal germicide). Avidin (5 mg) was added to the diluted latex and the resulting suspension was rotated end-over-end at 37° C. for 24 hours. The avidin was thereby attached to the particles through the chloromethyl groups on the particle surfaces. Biotin binding capacity, as measured by the procedure described in Example 1, was $1.5 \times 10^{-6}$ molar sites per 0.3% of diluted particle suspension.

EXAMPLE 5

Preparation of Reagent Having Biotin Attached to the Particles and Use in an Assay for hCG This example demonstrates the preparation of an immunoreactive reagent of this invention whereby biotin is attached to water-insoluble polymeric particles, and the use of the reagent in an assay for hCG.

Preparation of Reagent

A solution of borate buffer (50 ml, 0.05 molar, pH 8.5) containing 0.01% thiomersal germicide was placed in a centrifuge tube, followed by the addition of a solution (6 ml) of casein (1 mg/ml) in deionized distilled water. The tube was capped and shaken vigorously, then an aqueous dispersion (1.23 ml of 12.22% solids) of poly(styrene-co-m & p-chloromethylstyrene) (77.3:22.7 molar ratio) polymeric particles (average size about 2.7 μm) was added, and the tube was capped and rotated end-over-end for 24 hours at 37° C. The resulting particles had casein attached to the outer surfaces through the reactive chloromethyl groups.

The casein-particle reagent was then washed with glycine buffer (0.1 molar, pH 8.5) containing 0.01% thiomersal, and then resuspended in glycine buffer (0.1 molar) containing 0.01% thiomersal to produce a dispersion (0.3% solids) of a casein-particle reagent.

A sample of the dispersion just described (100 ml) was centrifuged, washed with sodium bicarbonate solution (80 ml, 100 mmolar), centrifuged again at about 15,000 rpm for 5 to 6 minutes, and resuspended in sodium bicarbonate (100 mmolar) to produce a 100 ml bead suspension. This suspension was treated with a mixture of biotin esterified with N-hydroxysuccinimide (10 mg), and allowed to incubate for about 90 minutes. The resulting product was centrifuged, washed with sodium phosphate buffer (200 ml, 50 mmolar, pH 7.2) containing diethylenetriaminepentaacetic acid (5 μm), centrifuged again and resuspended in sodium phosphate (100 ml, 50 mmolar, pH 7.2, 0.3% solids).

Assay for hCG

A three-well test device like that described in U.S. Pat. No. 4,870,007 of Smith-Lewis (noted above) was pretreated by contacting the nylon microporous filter in two of the wells with a solution of succinylated casein (2% solids). The membrane in the third test well was not so treated.

A stock solution of hCG (GC-10 chorionic gonadotropin from Sigma Chemical Co.) was prepared with phosphate buffered saline solution (50 mmolar sodium phosphate, 150 mmolar sodium chloride, pH 7) to comprise 5000 mI.U. hCG/ml for use as a test solution.

A sample (150 μl) of this test solution was placed in each of the two casein-treated test wells of the test device, and the following reagents were immediately placed in each of the three wells:

a) 40 μl of the biotinylated reagent described above, diluted 1:10.

b) 40 μl of an avidin-anti-hCG conjugate diluted 1:200. This conjugate was prepared from a purified monoclonal antibody against β-hCG (Immunoresearch) coupled to thiolated avidin by the thiol/maleimide procedure of Chen et al, Clin. Chem., 30(9), pp. 1446-1451 (1984) having 0.01% thiomersal added. The solution was characterized as having an optical density of 0.072 at 280 nm before dilution.

c) 40 μl of a peroxidase labeled monoclonal antibody against hCG diluted 1:250. This conjugate was prepared by coupling the antibody to horseradish peroxidase essentially as described by Chen et al, (noted above). The solution comprised 0.49 mg/ml of antibody before dilution.

The mixture in each test well was allowed to incubate for 30 seconds, then fluid was drained through the membrane, and each well was washed with 8 drops of a solution of sodium phosphate (100 mmolar) and sodium dodecylsulfate (10 mmolar). To each well was then added one drop of a dye composition prepared by mixing the following solutions A and B in a ratio of 500 ml of A to 5 ml of B.

Solution A:

sodium phosphate buffer (100 mmolar, pH 7),

1% poly(vinyl pyrrolidone) (MW=40,000), diethylenetriaminepentaacetic acid (5 mmolar) chelating agent, 4'-hydroxyacetanilide (5 mmolar) electron transfer agent, hydrogen peroxide (5 mmolar), adjusted to pH of 7 with sodium hydroxide.

Solution B:

Spectra grade methanol saturated with the leuco dye 4,5-bis(4-methoxyphenyl)-2-(3,5-dimethoxy-4-hydroxyphenyl)imidazole.

After incubation for 15 seconds, the fluid was drained through the membrane in each test well, and the color formed on the membrane was observed after another three minutes. The color formed was indicative of the presence of hCG in the test solution.

The assay described above was repeated twice except that the fluid was drained in each test well after 15 minutes incubation, followed by color observation after one or two minutes. Also, in the third assay, the biotinylated reagent dispersion was used undiluted. The following table shows the results from these assays. These data show that a positive color is generated in the test wells containing the hCG test solution. However, in the third well into which no hCG was added, there was essentially no color formation.

TABLE I

| Assay | Test Well | Casein Pre-treatment | Incubation Time | Color Observed | | |
|---|---|---|---|---|---|---|
| | | | | 1 Min. | 2 Min. | 3 Min. |
| 1* | 1 | Yes | 30 sec. | — | — | Light Pink |
| 1* | 2 | Yes | 30 sec. | — | — | Light Pink |
| 1* | 3 | No | 30 sec. | — | — | White with Pink Edges |
| 2* | 1 | Yes | 15 min. | Medium Pink | Medium Pink (Mottled) | — |
| 2* | 2 | Yes | 15 min. | Medium Pink | Medium Pink | — |

TABLE I-continued

| Assay | Test Well | Casein Pre-treatment | Incubation Time | Color Observed 1 Min. | Color Observed 2 Min. | Color Observed 3 Min. |
|---|---|---|---|---|---|---|
| 2* | 3 | No | 15 min. | White | (Mottled) White with some Pink | — |
| 3** | 1 | Yes | 15 min. | — | Very Pale Pink | — |
| 3** | 2 | Yes | 15 min. | — | Very Pale Pink | — |
| 3** | 3 | No | 15 min. | — | White | — |

*Biotinylated Reagent Dispersion Diluted 1:10
**Biotinylated Reagent Dispersion Undiluted

EXAMPLE 6

Use of Reagent to Determine Leutinizing Hormone (LH)

Immobilization of Avidin on Particles

A solution (50 ml, 0.05 molar, pH 8.5) of borate buffer containing thiomersal germicide (0.01%) was placed in a polypropylene centrifuge tube, and to it was added 6 ml of a solution of egg white avidin (6 mg, Sigma Chemical Co.) dissolved in 6 ml of deionized distilled water. The tube was then capped and shaken vigorously, followed by addition of 1.35 ml of a dispersion (15.5% solids) of poly[styrene-co-m & p-(2-chloroethylsulfonylmethyl)styrene] (95.5:4.5 molar ratio) beads (average size of 2.54 μmeters) and rotation end-over-end for 24 hours.

The polymer beads having avidin covalently attached thereto were washed with glycine buffer (0.1 molar, pH 8.5) containing 0.01% thiomersal, and then resuspended in glycine buffer (0.1 molar) containing 0.01% thiomersal to produce a dispersion containing an insoluble separation specific binding reagent (0.3% solids).

Assay for LH

A test device having three test wells like that described in U.S. Ser. No. 136,211 of Smith-Lewis (noted above), having a 5 μm mesh nylon filter membrane which had been pretreated with casein in each well, was used in this assay. Also used in the assay were: a biotinylated antibody to LH (0.044 mg/ml in phosphate buffered saline solution) prepared similarly to the biotinylated antibody to hCG described above, a horseradish peroxidase labeled antibody to LH (0.0015 mg/ml in phosphate buffered saline solution containing 0.5% bovine serum albumin), and the reagent described above comprising avidin on beads (concentrated to 0.9% solids, pH 8.5).

Several urine samples were tested in this assay:

(a) a sample collected the 13th day of a woman's menstrual cycle containing 18 mI.U. LH/ml, and (b) a sample collected the 14th day of the woman's menstrual cycle containing 64 mI.U. LH/ml.

Both of these samples were taken from the same person and the LH content was determined by an LH radioimmunoassay kit available from Diagnostic Products Corporation.

A mixture of urine sample (a) (200 ml), the peroxidase-labeled antibody (35 μl) and the biotinylated antibody (10 μl) was prepared and incubated at room temperature for two minutes. The insolubilized avidin reagent (40 μl) was then added to the mixture and incubation was continued for another five minutes. The mixture was then transferred to one of the test wells of the test device, and fluid and unreacted materials were drained away leaving insolubilized ternary complex formed during incubation on the filter membrane. The remaining insolubilized product was then washed twice with phosphate buffered saline solution (125 μl) containing 0.1% Tween 20 surfactant (a sorbitan monolaurate nonionic surfactant available from ICI Americas, Inc.), filtered again and then contacted with a dye-providing solution (50 μl, pH 7) like that described in U.S. Ser. No. 136,166 of McClune et al (noted above). This solution is prepared with 5 ml of 4,5-bis(4-methoxyphenyl)-2-(3,5-dimethoxy-4-hydroxyphenyl)imidazole leuco dye in methanol (15 mg/ml, mixed with 500 ml of a buffered solution of poly(vinyl pyrrolidone) (1% in 100 mmolar sodium phosphate), diethylenetriaminepentaacetic acid (5 mmolar) chelating agent, hydrogen peroxide (5 mmolar) and 4'-hydroxyacetanilide (5 mmolar) electron transfer agent.

Urine sample (b) was similarly assayed using a second test well of the test device.

In both test wells, a color was seen on the filter membrane within five minutes. The color in the first well was light pink in color whereas the color in the second well was bright red in color.

EXAMPLE 7

Assay for Streptococcus A Antigen

This example demonstrates the preparation and use of a reagent of this invention to determine Streptococcus A antigen in a fluid sample. It also demonstrates that this reagent is not useful for the determination of Streptococcus B antigen.

The reagent was prepared by attaching avidin to poly(styrene-co-m & p-chloromethylstyrene-co-2-hydroxyethyl acrylate) (69:30:1 molar ratio) particles (0.69 μmeters average size) using a procedure similar to that described in Example 1. The particles are also prepared using an emulsion polymerization procedure like that described in Example 1.

A sample (0.15% solids) of the reagent described above was mixed with a biotinylated antibody to Streptococcus A antigen (20% antibody w/w) and a fluid sample containing extracted Streptococcus A antigen, and the resulting mixture was incubated for 1 hour. After that time, it was observed that an agglutination reaction had occurred indicating that the antibody had reacted with the antigen, and the resulting complex was insolubilized by the reaction of avidin with biotin.

In contrast, no agglutination was observed in a similar assay when Streptococcus B antigen was substituted for Streptococcus A antigen.

EXAMPLE 8

Preparation of Reagent of the Invention

This example is similar to Example 1 and illustrates the preparation of a polymeric latex, and the attachment of avidin in the preparation of a reagent of this invention.

Preparation of Polymeric Latex

The three solutions outlined below were continuously added to a 1365 ml vessel containing deoxygenated water at 80° C. at the indicated rates:

Solution 1: Styrene (766 g), p-chloroacetamidostyrene (40 g) and 1-dodecanethiol (8.1 g) in methanol (210 g) at 2.3 g/min. for 316 minutes.

Solution 2: Ammonium persulfate (16.1 g) and distilled, deoxygenated water (1350 g) at 4.15 g/min. for 316 minutes.

Solution 3: Sodium pyrosulfite (8.1 g) and distilled water (1350 g) at 4.15 g/min. for 316 minutes.

After 316 minutes, the reaction was stopped, yielding about 1226 g of latex at 18.7% solids. The latex was dialyzed for 4 days to yield a latex having 1482 g and 13.9% solids at a pH of 4.8. Elemental analysis confirmed that the latex particles were formed from poly(styrene-co-p-chloroacetamidostyrene)(97.27:2.73 molar ratio). The resulting latex particles had an average diameter of about 1.12 μm as measured by transmission electron microscopy.

Preparation of Avidin-Bead Reagent

A sample of the polymeric latex described above (2.16 ml at 13.9% solids) was diluted to 20 ml with borate buffer (0.05 molar, pH 8.5) to which was added avidin (6 mg) in water (6 ml). The resulting suspension was agitated end-over-end at room temperature for 16 hours. The polymeric particles were then centrifuged twice and resuspended in glycine buffer (0.1 molar, pH 8.5). The reagent which resulted contained avidin covalently attached to the particles through the reactive halo groups on their outer surfaces.

Assay

An assay was performed on various urine specimens to which various amounts of hCG had been added. No hCG was added to one specimen. The assay was similar to that shown in Example 3 above in which two antibodies to hCG were used, one biotinylated, and the other labeled with peroxidase, and was carried out in a disposable test device having three test wells.

One test well of the disposable test device was used as a negative control, and the second, containing 400 mI.U. hCG, was used as a positive control. The third well was designated as the specimen test well.

The results of the assays are shown below in which the color readings for each test well are listed. It can be seen that the reagent of this Example acceptably detected even low levels of hCG in the specimens.

TABLE II

| hCG Amount (mI.U.) | Color Reading | | |
|---|---|---|---|
| | Negative Control | Test | Positive Control |
| 0 | 0 | 0 | 8 |
| 30 | 0 | 1 | 8 |
| 50 | 0 | 2 | 7.5 |
| 20,000 | 0 | 9 | 10 |
| 300,000 | 0 | 5.5 | 5 |

The invention has been described in detail with particular reference to preferred embodiments thereof, but it will be understood that variations and modifications can be effected within the spirit and scope of the invention.

We claim:

1. A water-insoluble reagent comprising:
   a polymeric particle comprising a polymer which is derived from one or more ethylenically unsaturated polymerizable monomers, at least one of which monomers has reactive groups which are selected from the group consisting of activated 2-substituted ethylsulfonyl, vinylsulfonyl and an active halogen atom,
   said particle being covalently attached through said reactive groups on the outer surface of said particle to a specific binding ligand selected from the group consisting of avidin, biotin and an avidin or biotin derivative.

2. The reagent of claim 1 wherein said particle contains a tracer material.

3. The reagent of claim 1 wherein said specific binding ligand is avidin or a derivative thereof.

4. The reagent of claim 1 wherein said specific binding ligand is biotin or a derivative thereof.

5. The reagent of claim 1 wherein said polymer is represented by the formula:

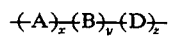

wherein

—A— represents recurring units derived from one or more hydrophobic ethylenically unsaturated polymerizable monomers, —B— represents recurring units derived from one or more ethylenically unsaturated polymerizable monomers having a reactive group selected from the group consisting of activated 2-substituted ethylsulfonyl, vinylsulfonyl and an active halogen atom, —D— represents recurring units derived from one or more ethylenically unsaturated polymerizable monomers other than those represented by —A— or —B—, x is from 0 to about 99.9 mole percent, y is from about 0.1 to about 100 mole percent, and z is from 0 to about 20 mole percent.

6. The reagent of claim 5 wherein x is from about 45 to about 99.5 mole percent, y is from about 0.5 to about 55 mole percent, and z is from 0 to about 10 mole percent in the defined polymer.

7. The reagent of claim 5 wherein said reactive group is haloalkyl of 1 to 3 carbon atoms.

8. The reagent of claim 5 wherein —B— represents recurring units derived from one or more ethylenically unsaturated monomers represented by the formula:

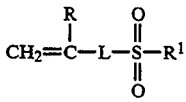

wherein
R is hydrogen or substituted or unsubstituted alkyl,
$R^1$ is —CH=CHR² or —CH₂CH₂X wherein X is a leaving group which is displaced by a nucleophile or is eliminated in the form of HX by treatment with a base, and R² is hydrogen, substituted or unsubstituted alkyl, or substituted or unsubstituted aryl, and
L is a linking group selected from the group consisting of substituted or unsubstituted alkylene, substituted or unsubstituted arylene, a combination of one or more of each of said alkylene and arylene groups, and said combinations interrupted or terminated with one or more amide or ester groups.

9. The reagent of claim 8 wherein said —B— recurring units are derived from the defined monomers wherein R is hydrogen or methyl, $R^1$ is —CH₂CH₂X and L is substituted or unsubstituted phenylenealkylene, carbonyliminoarylenealkylene, or carbonyliminoalkyleneiminocarbonylalkylene.

10. The reagent of claim 5 wherein
said —A— recurring units are derived from one or more of styrene, vinyltoluene, ethylene dimethacrylate, butyl acrylate, divinylbenzene, 2-ethylhexyl methacrylate and methyl methacrylate,
said —B— recurring units are derived from one or more of m & p-(chloromethyl)styrene, m & p-(2-chloroethylsulfonylmethyl)styrene, m & p-[2-(p-tolylsulfonyloxy)ethylsulfonylmethyl]styrene, m & p-vinylsulfonylmethylstyrene, N-[m- & p-(2-chloroethylsulfonylmethyl)phenyl]acrylamide, and N-[2-(2-chloroethylsulfonyl)ethylformamidomethyl]acrylamide, and
said —D— recurring units are derived from one or more of sodium 2-acrylamido-2-methylpropanesulfonate, sodium acrylate, sodium 3-acryloyloxypropane sulfonate, sodium methacrylate, 2-hydroxyethyl acrylate, 2,3-dihydroxypropyl acrylate, N-isopropylacrylamide, acrylamide and acrylonitrile.

11. The reagent of claim 1 wherein said particle comprises said polymer homogeneously throughout.

12. The reagent of claim 1 wherein said particle is a core/shell particle wherein said shell comprises said polymer having said reactive groups.

13. The reagent of claim 1 wherein said polymeric particle is one which has been prepared by emulsion polymerization without the use of surfactants or emulsifiers.

14. A method for the determination of a biological compound in an aqueous liquid comprising:
A. contacting said liquid with a water-insoluble reagent comprising:
a polymeric particle comprising a polymer which is derived from one or more ethylenically unsaturated polymerizable monomers, at least one of which monomers has reactive groups which are selected from the group consisting of activated 2-substituted ethylsulfonyl, vinylsulfonyl and an active halogen atom,
said particle being covalently attached through said reactive groups on the outer surface of said particle to a specific binding ligand selected from the group consisting of avidin, biotin and an avidin or biotin derivative,
B. forming a reaction product of said reagent with a receptor molecule conjugated to an immunoreactive species capable of immunological reaction with said biological compound for said specific binding ligand, which receptor molecule is or will be complexed with said biological compound, and
C. determining said biological compound as a result of the presence of said reaction product.

15. The method of claim 14 wherein said reagent comprises avidin, or a derivative thereof, which is reacted with said receptor molecule which is conjugated with an immunoreactive species capable of immunological reaction with said biological compound.

16. The method of claim 15 for the determination of hCG in said liquid wherein said immunoreactive species is a first antibody against hCG, and wherein said method is carried out with a second antibody against hCG which is labeled for detection.

17. The method of claim 16 wherein said second antibody is labeled with an enzyme.

18. The method of claim 16 wherein said second antibody is attached to a polymeric particle which has a detectable tracer material.

19. The method of claim 15 wherein said immunoreactive species is a monoclonal antibody.

20. The method of claim 14 wherein said particle contains a tracer material.

21. The method of claim 14 wherein said polymer is represented by the formula:

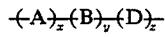

wherein
—A— represents recurring units derived from one or more hydrophobic ethylenically unsaturated monomers,
—B— represents recurring units derived from one or more ethylenically unsaturated monomers having a reactive group selected from the group consisting of activated 2-substituted ethylsulfonyl, vinylsulfonyl and an active halogen atom,
—D— represents recurring units derived from one or more ethylenically unsaturated monomers other than those represented by —A— or —B—,
x is from 0 to about 99.9 mole percent, y is from about 0.1 to about 100 mole percent, and z is from 0 to about 20 mole percent.

22. The method of claim 14 for the determination of HTLV-I, HTLV-II, HIV-I or HIV-II.

23. A method for the determination of a biological compound in an aqueous liquid comprising:
A. contacting said liquid with a water-insoluble reagent comprising:
a core/shell polymeric particle in which the shell comprises a polymer which is represented by the formula:

wherein
—A— represents recurring units derived from one or more hydrophobic ethylenically unsaturated monomers,
—B— represents recurring units derived from one or more ethylenically unsaturated monomers having a reactive group selected from the group consisting of activated 2-substituted ethylsulfonyl, vinylsulfonyl and an active halogen atom, —D— represents recurring units derived from one or more ethylenically unsaturated monomers other than those represented by —A— or —B—, x is from 0 to about 99.9 mole percent, y is from about 0.1 to about 100 mole percent, and z is from 0 to about 20 mole percent, said particle being covalently attached through said reactive groups on the outer surface of said shell to avidin or a derivative thereof, B. forming a reaction product of said reagent with a biotinylated reagent comprised of biotin or a derivative thereof attached to a first receptor molecule for said biological compound so as to form an insoluble specific binding complex between avidin and said biotinylated reagent, C. prior to, simultaneously with or subsequent to said contacting step A, contacting said biological compound with a second receptor molecule which is capable of participating in a specific binding reaction with said biological compound but which is not reactive with said first receptor molecule, said second receptor being labeled with a detectable tracer material, so as to form a labeled insoluble complex, and D. detecting said labeled insoluble complex to indicate the presence of said biological compound.

24. The method of claim 23 wherein said biological compound is an antigen and said first and second receptors are distinct antibodies to said antigen.

25. The method of claim 23 wherein said biological compound is an antibody, said first receptor is an antigen reactive with said compound, and said second receptor is an antibody directed against said compound.

* * * * *